United States Patent [19]

Yamanaka et al.

[11] Patent Number: 5,606,096

[45] Date of Patent: Feb. 25, 1997

[54] PRODUCTION OF UNSATURATED CARBAMIC ACID DERIVATIVE

[75] Inventors: Eiji Yamanaka, Suita; Noriyuki Tsuboniwa, HigashiOsaka; Takao Morimoto, Katano; Masamichi Furukawa, Neyagawa; Satoshi Urano, Tsuzuki-gun, all of Japan

[73] Assignee: Nippon Paint Co., Ltd., Osaka, Japan

[21] Appl. No.: 417,431

[22] Filed: Apr. 3, 1995

Related U.S. Application Data

[63] Continuation of Ser. No. 20,824, Feb. 19, 1993, abandoned.

[30] Foreign Application Priority Data

Feb. 20, 1992 [JP] Japan .................................... 4-033139

[51] Int. Cl.⁶ ................................................ C07C 261/00
[52] U.S. Cl. .......................... 560/157; 544/168; 546/226; 549/496; 560/165; 560/166; 560/167; 564/48; 564/56; 564/60; 564/62; 564/255
[58] Field of Search ................................ 560/157, 165, 560/167, 166; 549/496

[56] References Cited

U.S. PATENT DOCUMENTS

| | | | |
|---|---|---|---|
| 2,917,535 | 12/1959 | Britton | 560/157 |
| 2,934,559 | 4/1960 | Beinfest | 560/157 |
| 3,173,941 | 3/1965 | Levy | 560/157 |
| 3,219,686 | 11/1965 | Beinfest | 560/157 |
| 3,853,960 | 12/1974 | Crowther | 560/157 |
| 3,856,816 | 12/1974 | Nikles | 560/157 |
| 3,896,088 | 7/1975 | Raynolds | 560/157 |
| 4,001,191 | 1/1977 | Reed | 560/157 |
| 4,279,833 | 7/1981 | Culbertson | 560/157 |
| 4,335,138 | 6/1982 | Wiersdorff | 560/157 |
| 4,663,472 | 5/1987 | Green | 560/157 |
| 4,758,475 | 7/1988 | Eckes | 560/157 |
| 4,935,413 | 6/1990 | Urano | 560/157 |
| 5,187,306 | 2/1993 | Tsuboniwa | 560/157 |
| 5,235,062 | 8/1993 | Greco | 560/157 |

FOREIGN PATENT DOCUMENTS

| | | |
|---|---|---|
| A0066922 | 5/1982 | European Pat. Off. . |
| A0177122 | 7/1984 | European Pat. Off. . |
| A0465162 | 6/1991 | European Pat. Off. . |

OTHER PUBLICATIONS

Adams, Chemical Reviews, 65, pp. 567–602 (1965).

*Primary Examiner*—Michael L. Shippen
*Attorney, Agent, or Firm*—Townsend & Banta

[57] ABSTRACT

The present invention provides a process for producing a variety of unsaturated carbamic acid derivatives from corresponding unsaturated carbamates by substitution reaction. The present invention provides a process for producing unsaturated carbamic acid derivatives, comprising reacting an unsaturated carbamate represented by

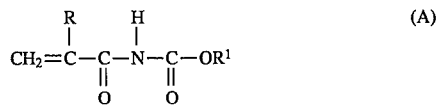

wherein R represents a hydrogen atom or an alkyl group having 1 to 8 carbon atoms, $R^1$ represents a residue of an alcohol from which an OH group is removed,
with an alcohol, a primary or secondary amine or an oxime at a temperature of 80° to 150° C. to substitute the $-OR^1$ group in the formula (A).

8 Claims, No Drawings

PRODUCTION OF UNSATURATED CARBAMIC ACID DERIVATIVE

CROSS REFERENCE TO A RELATED APPLICATION

This is a file wrapper continuation application of application Ser. No. 08/020,824, filed Feb. 19, 1993, now abandoned.

FIELD OF THE INVENTION

The present invention relates to a process for producing unsaturated carbamic acid derivatives from corresponding unsaturated carbamates by substitution reaction.

BACKGROUND Of THE INVENTION

The present inventors have already proposed carbamic acid esters represented by:

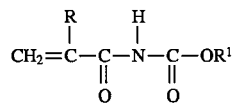

wherein R represents a hydrogen atom or an alkyl group having 1 to 8 carbon atoms, $R^1$ represents a residue of an alcohol from which an OH group is removed,
and also proposed their applications (Japanese Kokai Publications 61-275259, 61-275260 and 61-275270 corresponding to U.S. Pat. No. 4,935,413).

Japanese Kokai Publication 4-66563 (corresponding to EP-A 465,162) discloses a one step synthesis method wherein the unsaturated carbamic acid esters are prepared by reacting methacrylamide and chloroformic acid ester. However, the chloroformic acid esters are unstable and a few kind of them can be used therefor.

Japanese Kokai Publication 61-275259 also provides a process for producing the unsaturated carbamic acid esters wherein a compound having an isocyanate group, represented by:

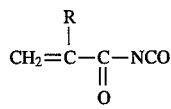

(wherein R is the same as mentioned above), is reacted with alcohols. The isocyanate compound, however, is too reactive to control and treat the reaction.

SUMMARY OF THE INVENTION

The present invention provides a process for producing a variety of unsaturated carbamic acid derivatives from corresponding unsaturated carbamates by substitution reaction. Thus, the present invention provides a process for producing unsaturated carbamic acid derivatives, comprising reacting. an unsaturated carbamate represented by

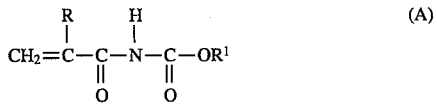

wherein R represents a hydrogen atom or an alkyl group having 1 to 8 carbon atoms, $R^1$ represents a residue of an alcohol from which an OH group is removed,
with an alcohol, a primary or secondary amine or an oxime at a temperature of 40° to 150° C. to substitute the —$OR^1$ group in the formula (A).

DETAILED DESCRIPTION OF THE INVENTION

There have not been known synthetic reactions which employ substitution reaction of acylcarbamates. Ester exchange reaction is already known to the art as one of similar reactions, but it necessitates relatively high temperatures as high as 180° C. or addition of catalyst to proceed reaction. It, however, is surprisingly found by the present inventors that the substitution reaction of the unsaturated carbamates represented by the formula (A) can be carried out at relatively low temperature, e.g. 40° to 150° C. and does not always need catalyst.

The unsaturated carbamates (A) used in the present invention can be obtained by any methods which are known to the art, including methods as described in Japanese Kokai Publications 61-275259 and 4-66563 (corresponding to U.S. Pat. No. 4,935,413 and EP-A 465,162), and the method as explained hereinafter.

In the formula (A), R represents a hydrogen atom or an alkyl group having 1 to 8 carbon atoms, preferably an alkyl group having 1 to 2 carbon atoms (e.g. methyl or ethyl group). $R^1$ is a residue of an alcohol from which an OH group is removed, including an alkyl group having 1 to 18 carbon atoms, an aryl group having 6 to 15 carbon atoms and an aralkyl group having 7 to 15 carbon atoms. The substitution reaction of the present invention can produce a desired product by shifting equilibrium of reaction. For example, when equilibrium of reaction is shifted by distilling an alcohol of $R^1$—OH away, it is preferred that the $R^1$ group is an alkyl group having relatively low carbon number especially 1 to 6 carbon atoms.

The reactant to be reacted with the unsaturated carbamates includes an alcohol a primary or secondary amine or an oxime. Examples of the alcohols are an alkyl alcohol having 1 to 30 carbon atoms which may be substituted with halogen atoms, such as methanol, ethanol, propanol, isopropanol, butanol, iauryl alcohol, stearyl alcohol and triacontanol; an alkenyl alcohol having 3 to 20 carbon atoms, such as allyl alcohol, crotyl alcohol and phytol; an aralkyl alcohol having 7 to 16 carbon atoms, such as benzyl alcohol, phenethyl alcohol and 8-phenyl menthol; an aralkenyi alcohol having 9 to 18 carbon atoms, such as cinnamyl alcohol; a polyhydric alcohol, such as ethylene glycol, diethylene glycol, hexanediol and trimethylolpropane; and the like. The alcohols can also be those having at least on hatarc atoms in molecule and having a molecular weight 60 to 1,000, including an alcohol having ether bond, such as methoxyethanol, butoxyethanol, hexyloxyethanol, methoxybutanol, furfuryl alcohol, tetrahydrofurfuryl alcohol and polyethylene glycol; an alcohol having an ester group, such as ethyleneglycol monoacetate and 2-hydroxyethyl methacrylate; an alcohol having tertiary nitrogen, such as N,N-dimethylaminoethanol and 2-pyridylcarbinol; an alcohol having a thioether group, such as 3-methylthio-1-hexanol, methyl thiopropanol and 2-(2-thienyl)ethanol; an alcohol having a halogen atom, such as 2-fluoroethanol, 2,2,3,3,3-pentafluoro-1-propanol, 2-chloroethanol, 2,2-dichloroethanol, 2,2,2-trichloroethanol, 1,3-dichloro-2-propanol, 3-bromo-1-propanol, 1-bromo-2-propanol and 2-iodoethanol; and the like. The above mentioned alcohol may also be substituted with one or more substituents (e.g. a nitro group, a nitrile group, a sulfonate group, a phosphate group and an aldehyde group). If a monohydric alcohol among the above alcohols is indicated as $R^2$—OH, the $R^2$ group may be the same as the $R^1$ group, but generally the $R^1$ group has smaller number of carbon atoms than the $R^2$ group and the alcohol ($R^1$—OH) has lower boiling point than the $R^2$—OH alcohol, in view of equilibrium shift. The $R^2$ group preferably has 3 to 30 carbon atoms and higher boiling point.

The primary or secondary amine employed in the present invention can be indicated by $R^3R^4$—N—H wherein $R^3$ and $R^4$ respectively show a hydrogen atom, an alkyl or alicyclic group having 1 to 18 carbon atoms, an aryl group having 6 to 15 carbon atoms, an aralkyl group having 6 to 15 carbon atoms and the like, provided that neither $R^3$ nor $R^4$ is a hydrogen atom. Typical examples of the primary and secondary amines are alkylamines, such as methylamine, ethylamine, propylamine, isopropylamine, laurylamine and stearytamine; an aralkylamine, such as benzylamine and phenethylamine; a dialkylamine, such as dimethylamine, diethylamine and dipropylamine; a dicycloalkylamine, such as dicyclopentylamine and dicyclohexylamine; an alkylaralkylamine, such as methylbenzylamine, methylphenetylamine; a cyclic amine, such as aniline, tiazoleamine, piperidine, morpholine, aziridine; and the like.

The oxime employed in the present invention is a compound represented by $R^5R^6$—C=N—OH, wherein $R^5$ and $R^6$ respectively show a hydrogen atom, an alkyl group having 1 to 12 carbon atoms, an alkenyl group having 2 to 8 carbon atoms,. an alkynyl group having 2 to 8 carbon atoms, an aryl group having 6 to 12 carbon atoms and the like, $R^5$ and $R^6$ may bond to form an alkylene group having 4 to 8 carbon atoms, provided that neither $R^5$ nor $R^6$ is a hydrogen atom. Typical examples of the oximes are alkane aidehyde oximes, such as acetoaldehyde oxime; alkene aidehyde oximes; dialkyl ketone oximes, such as phenyl aidehyde oxime, acetone oxime, methyl ethyl ketone oxime and methyl isobutyl ketone oxime; dialkenyl ketone oxime; alkyl alkenyl ketone oximes; phenyl alkyl ketone oximes, such as phenyl methyl ketone oxime; lower alkanoyl acetone oximes, such as acetyl acetone oxime; cycloalkanone oximes, such as cyclopenetanone oxime and cyclohexanone oxime; and the like.

The reactant (alcohols and the like) may be employed in an amount of 0.5 to 5 equivalent, preferably 1 to 3 equivalent based on one equivalent of the unsaturated carbamate (A). The above range is not limited, because it is possible that the reactant is used in a very large amount to shift equilibrium of reaction.

The reaction may be conducted in an inert solvent if necessary. The inert solvent is not limited as long as it does not adversely affect on the reaction, including an aliphatic hydrocarbon, such as pentane, heptane and hexane; an aromatic hydrocarbon, such as benzene, toluene and xylene; an alicyclic hydrocarbon, such as cyclohexane, methylcyclohexane and decaline; petroleum ether; petroleum benzine; a hydrocarbon halide, such as carbon tetrachloride, chloroform and 1,2-dichloroethane; an ether, such as ethyl ether, isopropyl ether, anisole, dioxane and tetrahydrofuran (THF); a ketone, such as acetone, methyl ethyl ketone, methyl isobutyl ketone, cyclohexanone, acetophenone and isophorone; an ester, such as ethyl acetate and butyl acetate; acetonitrile; dimethylformamide (DMF); dimethylsulfoxide; a mixture thereof and the like.

The reaction can be conducted at a temperature of 40° to 150° C., preferably 60° to 140° C. If temperature is low, the reaction would not proceed and if it is high, side reaction would occur.

The reaction time is not limited, generally within the range of 0.1 to 10 hours, preferably 1 to 6 hours. The time, of course, widely varies depending upon reactivity of the reactants, reaction temperature and the like.

If necessary, a polymerization inhibitor may be added the reaction system, in order to inhibit polymerization through unsaturated double bonds. Typical examples of the polymerization inhibitors are hydroquinone, p-methoxyphenol, 2,6-di-t-butyl-4-methylphenol, 4-t-butylcatechol, bis-dihydroxybenzylbenzene, 2,2'-methylenehis )6-t-butyl-3-methylphenol), 4,4-butylidenebis(6-t-butyl-3-methylphenol), 4,4'-thiobis(6-t-butyl-3-methylphenol), p-nitrosophenol, diisopropylxanthogenesulfide, N-nitrosophenyihydroxyamine ammonium salt, 1,1-diphenyl-2-picrylhydrazile. 1,3,5-triphenylpheldazile, 2,6-di-t-butyl-α-(3, 5-di-butyl-4-oxo-2,5-cyclohexadiene-1-ilidene)-p-trioxy, 2,2,6,6-tetramethyl-4-piperidone-1-oxyl, dithiobenzoylsulfide, p,p'-ditolyltrisulfide, p,p'-ditolyltetrasulfide. dibenzyltetrasulfide, tetraethylthiuramdisulfide, phenotiazine and the like.

The reaction may be accelerated by a catalyst if necessary. Typical examples of the catalysts are tertiary amines, such as triethytamine, tributylamine and pyridine; acids, such as sulfuric acid, nitric acid, chloric acid, phosphoric acid and acetic acid; metal catalysts, such as lead acetate, cobalt acetate, nickel acetylacetonate, copper naphthenate and manganese acetylacetonate; and the like. An amount of the catalyst is not limited, but generally within the range of 0.001 to 0.1 equivalent based on the reactant.

The reaction product may be separated or isolated by art-known purifying methods. The resulting unsaturated carbamic acid derivatives are those represented by:

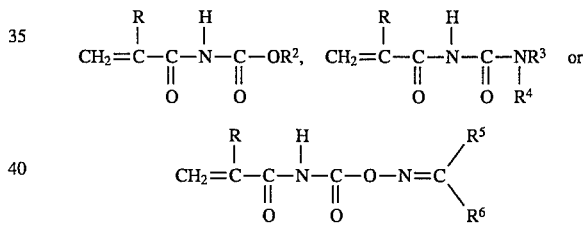

wherein $R^1$ to $R^6$ are the same as mentioned above.

According to the present invention, many carbamic acid derivatives can be obtained from unsaturated carbamates by substitution reaction. It is advantageous that the reaction basically proceeds without high temperature and catalyst.

EXAMPLES

The present invention is illustrated by the following Examples which, however, are not to be construed as limiting the present invention to their details.

Example 1

A reaction vessel was charged with 15.7 g of ethyl N-methacryloylcarbamate and 52 g of 2-ethylhexyl alcohol, to which 0.1 g of hydroquinone was added and heated at 120° C. for one hour. The resulting mixture was condensed under reduced pressure and isolated by column chromatography to obtain 17.4 g of 2-ethylhexyl N-methacryloylcarbamate having a viscosity of 800 cp.

Example 2

A reaction vessel was charged with 14.3 g of methyl N-methacryloylcarbamate and 27 g of 1-octadecanol, to which 0.02 g of hydroquinone and 50 g of toluene were added and reacted at 117° C. for two hours with distilling toluene/methanol solution away. The resulting mixture was condensed under reduced pressure and isolated by column chromatography to obtain 32.8 g of white solid having a melting point of 38°–41° C.

Example 3

A reaction vessel was charged with 15.7 g of ethyl N-methacryloylcarbamate and 17.7 g of 2-butoxyethanol, to which 25 g of toluene were added and reacted at 118° C. for one hour with distilling toluene/ethanol solution away. The resulting mixture was condensed under reduced pressure and isolated by column chromatography to obtain 16.1 g of white solid having a melting point of 27°–28° C.

Example 4 to 6

Reaction products were obtained as generally described in Example 3, with the exception that the condition and reactants as described in Table 1 were employed.

TABLE 1

| Example No. | Carbamates | Amount | Reactant | Amount | Solvent | Reaction product | Yield | Melting point |
|---|---|---|---|---|---|---|---|---|
| 4 | Ethyl N-methacryloyl-carbamate | 15.7 g | Methanol | 16.2 | Butyl acetate | Methyl N-methacryloyl-carbamate | 14 g | 109–110° C. |
| 5 | Ethyl N-methacryloyl-carbamate | 78.5 g | Isopropyleneglycol monomethyl ether | 67.6 g | Methyl isobutyl ketone | 2-Methoxy-isopropyl N-methacryloyl-carbamate | 76.2 g | 84–86° C. |
| 6 | Ethyl N-methacryloyl-carbamate | 78.5 g | 2-Acetyl-t-butyl alcohol | 87.1 | Methyl isobutyl ketone | 2-Acetyl-t-butyl N-methacryloyl-carbamate | 33.8 g | 54–56° C. |

Example 7

A reaction vessel was charged with 78.5 g of ethyl N-methacryloylcarbamate and 53.5 g of benzylamine to which 100 g of toluene were added and heated at 100° C. for 30 minutes, The resulting mixture was condensed under reduced pressure and isolated by column chromatography to obtain 46.4 g of N-benzyl-N'-methacryloyl urea having a melting point of 96°–98° C.

Example 8

A reaction vessel was charged with 78.5 g of ethyl N-methacryloylcarbamate and 46.5 g of aniline to which 100 g of toluene were added and heated at 120° C. for 30 minutes. The resulting mixture was condensed under reduced pressure and isolated by column chromatography to obtain 46.4 g of N-methacryloyl-N'-phenyl urea having a melting point of 165° to 166° C.

Example 8

A reaction vessel was charged with 7.8 g of ethyl N-methacryloylcarbamate and 20 g of acetone oxime, to which 20 g of ethyl acetate was added and heated at 82° C. for 10 minutes. After cooling, it was column-purified to obtain 1.3 g of 2-propyleneimino N-methacryloylcarbamate having a melting point of 31° to 32° C.

Examples 10 to 43

Reaction products were obtained as generally described in Example 3, with the exception that the conditions and reactants as described in Table 2 were employed.

TABLE 2

| No | Carbamates | Amount | Reactant | Amount | Solvent | Reaction product | yield | m.p. |
|---|---|---|---|---|---|---|---|---|
| 10 | Ethyl N-methacryloyl-carbamate | 15.7 g | Allyl alcohol | 8.7 g | Methyl isobutyl ketone | Allyl N-methacryloyl-carbamate | 13.9 g | 43–44° C. |
| 11 | ↑ | ↑ | Propargyl alcohol | 8.4 g | ↑ | Propargyl N-methacryloylcarbamate | 10.9 g | 92–94° C. |
| 12 | ↑ | ↑ | Benzyl alcohol | 16.2 g | ↑ | benzyl N-methacryloyl-carbamate | 19.3 g | 109–110° C. |
| 13 | ↑ | ↑ | Cynnamyl alcohol | 20.1 g | ↑ | Cynnamyl N-methacryloyl-carbamate | 15.9 g | 66–67° C. |
| 14 | ↑ | ↑ | 2-Hexyloxyethanol | 21.9 g | ↑ | 2-Hexyloxyethanol N-methacryloylcarbamate | 23.6 g | 25–26° C. |
| 15 | ↑ | ↑ | 3-Methoxybutanol | 15.6 g | ↑ | 3-Methoxybutyl N-methacryloylcarbamate | 18.3 g | 37–38° C. |
| 16 | ↑ | ↑ | Furfuryl alcohol | 14.6 g | 1,4-Dioxane | Furfuryl N-methacryloyl-carbamate | 16.0 g | 121–122° C. |
| 17 | ↑ | ↑ | Tetrahydrofur-furylalcohol | 15.2 g | ↑ | Tetrahydrofurfuryl N-methacryloylcarbamate | 14.4 g | 68–70° C. |
| 18 | n-Butyl-N-methacryloyl-carbamate | ↑ | Methyl glycolate | 13.5 g | 1,2-Dichloro-ethane | 1,2-Dichloroethane Methoxycarbonylmethyl N-methacryloylcarbamate | 11.1 g | 82–83° C. |
| 19 | Ethyl-N-methacryloyl-carbamate | ↑ | N,N-Dimethylamino-ethanol | 13.4 g | ↑ | N,N-Dimethylaminoethyl N-methacryloylcarbamate | 16.6 g | 71–73° C. |
| 20 | ↑ | ↑ | 1,1,1,3,3,3-Hexafluoro-2-propanol | 25.3 g | Toulene | 1,1,1,3,3,3-Hexafluoro-2-propyl N-methacryloylcarbamate | 25.2 g | 112–113° C. |
| 21 | ↑ | ↑ | 1,3-Dichloro-2-propanol | 19.3 g | ↑ | 1,3-Dichloro-2-propyl N-methacryloylcarbamate | 20.6 g | 101–102° C. |
| 22 | ↑ | ↑ | Stearylamine | 40.4 g | ↑ | N-methacryloyl-N'-stealylurea | 22.7 g | 38–41°C. |
| 23 | ↑ | ↑ | Dicyclohexyl-amine | 27.3 g | ↑ | N,N-Dicyclohexyl-N'-methacryloylurea | 20.0 g | 165–167° C. |
| 24 | n-Butyl-N-methacryloyl-carbamate | ↑ | Morpholine | 17.4 g | ↑ | N-Methacryloylmorpholine-carboxamide | 7.2 g | 104–105° C. |
| 25 | ↑ | ↑ | Allylamine | 8.6 g | ↑ | N-Allyl-N'-methacrylolurea | 6.7 g | 42–43° C. |
| 26 | ↑ | ↑ | Hexanediol | 5.9 g | ↑ | 1,6-bis(N-methacryloyl-carbamoyl)hexane | 10.9 g | yellow oil |
| 27 | n-Butyl-N-methacryloyl-carbamate | 15.7 g | phytol | 45 g | ↑ | 3,7,11,15-tetrametyl-2-hexadecenyl-N-methacryloyl-carbamate | 20.5 g | yellow oil |
| 28 | ↑ | ↑ | croly alcohol | 10.5 g | ↑ | 2-butenyl N-methacryl-carbamate | 14.6 g | ↑ |
| 29 | ↑ | ↑ | poly(etylene glycol)metyl ether (average M.W. 750) | 75 g | ↑ | Poly(ethylene grycol)mono-methylether N-methacryloyl-carbamate ether | 89 g | yellow wax |
| 30 | ↑ | ↑ | ↑(average M.W. 550) | 55 g | ↑ | ↑ | 75 g | ↑ |
| 31 | ↑ | ↑ | Phenethyl alcohol | 18.3 g | ↑ | Phenethyl N-methacryloylcarbamate | 18.2 g | white solid |
| 32 | ↑ | ↑ | Trimethiol propane | 13.4 g | ↑ | 1,1,1-tris(N-methacryloyl-carbanoylxymethyl)propane | 13.5 g | ↑ |
| 33 | ↑ | ↑ | Dipropylamine | 10.1 g | Toulene | N,N-Dipropyl-N'-methacryloylurea | 8.5 g | ↑ |
| 34 | ↑ | ↑ | Diethlamine | 7.1 g | ↑ | N,N-Diethyl-N'-methacryloylurea | 6.3 g | ↑ |
| 35 | ↑ | ↑ | Dicyclopentylamine | 15.3 g | ↑ | N,N-Dicyclopentyl-N'-methacryloylurea | 13.2 g | ↑ |
| 36 | ↑ | ↑ | Methlbenzylamine | 13.1 g | ↑ | N-benzyl-N-methyl-N'-methacryloylurea | 9.2 g | ↑ |
| 37 | ↑ | ↑ | Metylphenetyl-amine | 14.5 g | ↑ | N-methyl-N-phenetyl-N' methacryloylurea | 10.9 g | ↑ |
| 38 | ↑ | ↑ | Piperidine | 8.5 g | ↑ | N-methacryloyl-N'-piperidinourea | 6.3 g | ↑ |
| 39 | ↑ | ↑ | Methylisobutyl-ketone oxime | 25 g | ↑ | 4-methyl-2-pentyleneimino N-methacryloylcarbamate | 2.4 g | colorless oil c.p. 1400 |
| 40 | ↑ | ↑ | Metylphenyl-keloneoxime | 30 g | ↑ | 1-phenyl-1-ethyleneimino-N-methacryloylcarbamate | 2.5 g | m.p. 74–75° C. |
| 41 | ↑ | ↑ | Acetylacetone-oxime | 25 g | ↑ | 1-acetyl-2-propyleneimino-N-methacryloylcarbamate | 1.2 g | 85 . 97° C. |
| 42 | ↑ | ↑ | cyclopentanon-oxime | 25 g | ↑ | cyclopentyleneimino-N-methacryloylcarbamate | 1.3 g | 75–77° C. |
| 43 | ↑ | ↑ | cyclohexanen-oxime | 25 g | ↑ | cyclohexyleneimino-N-methacryloylcarbamate | 1.8 g | 86–88° C. |

What is claimed is:

1. A process for producing unsaturated carbamic acid derivative consisting essentially of reacting in the absence of a catalyst an unsaturated carbamate represented by:

$$\underset{O\quad\ O}{\underset{\|\quad\ \|}{CH_2=C-C-N-C-OR^1}}\overset{R\quad H}{\underset{|\quad\ |}{}} \quad (A)$$

wherein R represents a hydrogen atom or an alkyl group having 1 to 8 carbon atoms, $R^1$ represents a residue of an alcohol from which an OH group is removed, with an alcohol selected from the group consisting of an alkyl alcohol having 1 to 30 carbon atoms, an alkenyl alcohol having 3 to 20 carbon atoms, an aralkyl alcohol having 7 to 16 carbon atoms, an aralkenyl alcohol having 9 to 18 carbon atoms, an alcohol having at least one hetero atom in molecule and having a molecular weight of 60 to 1,000, at a temperature of 40° to 150° C. to substitute the $-OR^1$ group in the formula (A).

2. The process for producing an unsaturated carbamic acid derivative according to claim 1, wherein said $R^1$ is an alkyl group having 1 to 18 carbon atoms, an aryl group having 6 to 15 carbon atoms and an aralkyl group having 7 to 15 carbon atoms.

3. The process for producing an unsaturated carbamic acid derivative according to claim 1, wherein said alcohol to be reacted with the unsaturated carbamate (A) is present in an amount of 0.5 to 5 equivalent based on one equivalent of the unsaturated carbamate (A).

4. The process for producing an unsaturated carbamic acid derivative according to claim 1, wherein said reaction is conducted in the presence of a polymerization inhibitor.

5. A process for producing unsaturated carbamic acid derivative represented by:

$$\underset{O\quad\ O}{\underset{\|\quad\ \|}{CH_2=C-C-N-C-OR^2,}}\overset{R\quad H}{\underset{|\quad\ |}{}}$$

wherein R represents a hydrogen atom or an alkyl group having 1 to 8 carbon atoms, and $R^2$ represents an alcohol from which —OH group is removed, the alcohol being selected from the group consisting of an alkyl alcohol having 1 to 30 carbon atoms, an alkenyl alcohol having 3 to 20 carbon atoms, an aralkyl alcohol having 7 to 16 carbon atoms, an aralkenyl alcohol having 9 to 18 carbon atoms, an alcohol having at least one hetero atom in molecule and having a molecular weight of 60–1,000, consisting essentially of reacting in the absence of a catalyst and an unsaturated carbamic represented by:

$$\underset{O\quad\ O}{\underset{\|\quad\ \|}{CH_2=C-C-N-C-OR^1}}\overset{R\quad H}{\underset{|\quad\ |}{}} \quad (A)$$

wherein R represents a hydrogen atom or an alkyl group having 1 to 8 carbon atoms, and $R^1$ represents a residue of an alcohol from which an OH group is removed, with an alcohol selected from the group consisting of an alkyl alcohol having 1 to 30 carbon atoms, an alkenyl alcohol having 3 to 20 carbon atoms, an aralkyl alcohol having 7 to 16 carbon atoms, an aralkenyl alcohol having 9 to 18 carbon atoms, an alcohol having at least one hetero atom in molecule and having a molecular weight of 60 to 1,000, at a temperature of 40° to 150° C. to substitute the $-OR^1$ group in the formula (A).

6. The process for producing an unsaturated carbamic acid derivative according to claim 5, wherein said $R^1$ is an alkyl group having 1 to 18 carbon atoms, an aryl group having 6 to 15 carbon atoms, and an aralkyl group having 7 to 15 carbon atoms.

7. The process for producing an unsaturated carbamic acid derivative according to claim 5, wherein said alcohol to be reacted with the unsaturated carbamate (A) is present in an amount of 0.5 to 5 equivalent based on one equivalent of the unsaturated carbamate (A).

8. The process for producing an unsaturated carbamic acid derivative according to claim 5, wherein said reaction is conducted in the presence of a polymerization inhibitor.

* * * * *